United States Patent [19]

Kaneko et al.

[11] 4,236,828
[45] Dec. 2, 1980

[54] METHOD FOR CALIBRATING DENSITOMETER OF CATAPHORETIC APPARATUS AND CALIBRATION FILM FOR USE IN SUCH CALIBRATING METHOD

[75] Inventors: Nobutaka Kaneko; Ryo Fujimori, both of Hachioji

[73] Assignee: Olympus Optical Co., Ltd., Tokyo, Japan

[21] Appl. No.: 908,788

[22] Filed: May 23, 1978

[30] Foreign Application Priority Data

May 26, 1977 [JP] Japan .................................. 52-60527

[51] Int. Cl.³ ........................................... G01N 21/06
[52] U.S. Cl. ..................................... 356/444; 356/243
[58] Field of Search ................. 356/434, 443, 444, 243

[56] References Cited

U.S. PATENT DOCUMENTS

| | | |
|---|---|---|
| 3,669,543 | 6/1972 | Vaccaro ................................ 356/434 |
| 3,752,995 | 8/1973 | Liedholz ............................... 356/434 |
| 3,817,632 | 6/1974 | Picunko et al. ....................... 356/434 |
| 3,994,593 | 11/1976 | Kato et al. ............................ 356/444 |
| 3,995,959 | 12/1976 | Shaber .................................. 356/443 |
| 4,043,676 | 8/1977 | Holzinger et al. ................... 356/434 |

Primary Examiner—John K. Corbin
Assistant Examiner—R. A. Rosenberger
Attorney, Agent, or Firm—Haseltine and Lake

[57] ABSTRACT

In a method for calibrating or checking a densitometer section of a cataphoretic apparatus use is made of a calibration film comprising a transparent and flexible sheet and a pattern applied on the sheet and having a known density and the calibration film is fed into the densitomater with the aid of a mechanism for feeding usual sample bearing films. After the calibration for the densitometer has been completed using the introduced calibration film the film is discharged out of the densitometer with the aid of a mechanism for discharging the usual sample bearing films.

5 Claims, 5 Drawing Figures

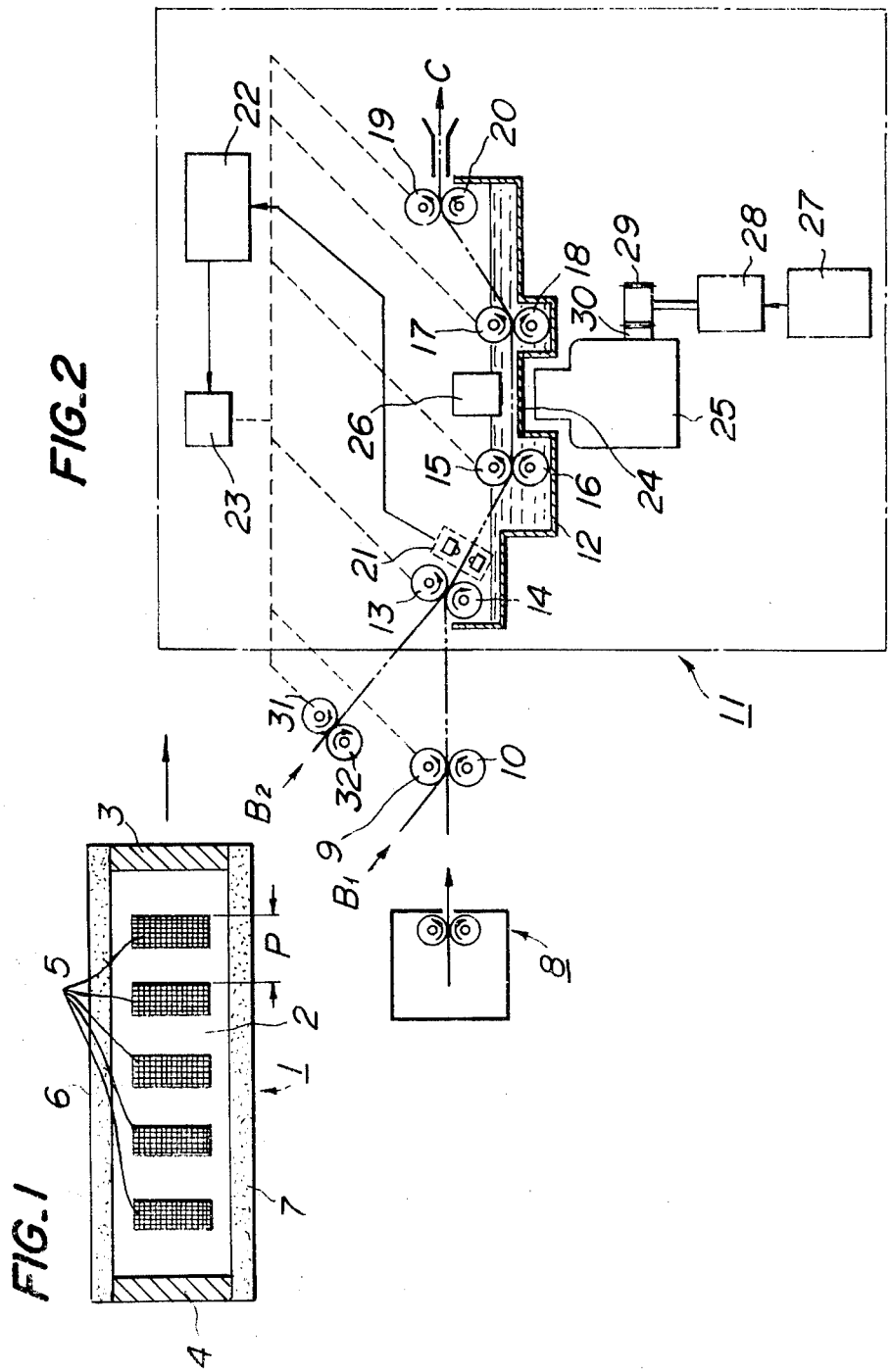

METHOD FOR CALIBRATING DENSITOMETER OF CATAPHORETIC APPARATUS AND CALIBRATION FILM FOR USE IN SUCH CALIBRATING METHOD

BACKGROUND OF THE INVENTION

1. Field of the Invention

The present invention relates to a cataphoretic analyzing technique, and more particularly to a method for calibrating or checking a densitometer for use in a cataphoresis apparatus for analyzing a serum protein with using a cellulose acetate film as a buffer solution bearing film.

2. Description of the Prior Art

A cataphoresis apparatus using a cellulose acetate film has several advantages, that is, lessening of adsorption of a sample or pigment, a capability of analyzing even very small amount of the sample because of lowering of the sample due to the lessening of adsorption of the sample, and an avairability of quantitative analysis because of clear fraction due to small tailing in a cataphoretic process. An automatic cataphoretic apparatus capable of simultaneously making cataphoretic process using cellulose acetate films to the plurality of samples has been described in U.S. Pat. No. 3,999,505. Such automatic cataphoretic apparatus comprises a section for cutting a bearing film roll into a separate film of a predetermined length, a section for wetting the bearing film with a buffer solution, a section for applying a serum sample on the bearing film, a cataphoretic section for fractionating the serum sample applied on the bearing film into components, a section for dyeing the bearing film which is subjected to the cataphoretic process, a section for decolorizing the bearing film, a section for drying the decolorized bearing film, a section for making the film transparent with a clarifying solution and a densitometer section for densitometrically measuring contents of serum protein. In such an apparatus it is sometimes required to calibrate or check the operation of the densitometer with using a calibration film or test film in order to increase the accuracy of measurement. In the known apparatus when the densitometer is to be calibrated, at first the densitometer is decomposed and the clarifying solution such as decalin is drawn off and then the test film is charged. However such a checking process is very cumbersome and expensive.

SUMMARY OF THE INVENTION

The present invention has for its object to provide an improved method for calibrating in a simple manner the densitometer in the cataphoresis apparatus without decomposing the densitometer.

In a calibrating method according to the invention use is made of a calibration film which has a pattern of known density and has substantially same configuration as a usual sample bearing film, the calibration film is fed to a photoelectrically measuring position with the aid of a mechanism which is used for feeding the usual sample bearing film, and after the measurement the calibration film is discharged from the densitometer with the aid of a mechanism for discharging the usual sample bearing film.

The present invention also relates to a calibration film for use in a method for calibrating the densitometer of the cataphoretic apparatus.

A calibration film according to the invention comprises a transparent and flexible sheet member and a pattern of known density applied on the sheet member, the calibration film having substantially same configuration as the usual sample bearing film.

BRIEF DESCRIPTION OF THE DRAWINGS

FIG. 1 is a plan view showing an embodiment of a calibration film according to the invention;

FIG. 2 is a schematic view illustrating a densitometer section for use in a cataphoretic apparatus, for which densitometer the calibrating method according to the invention is to be effected;

DESCRIPTION OF THE PREFERRED EMBODIMENTS

Figure 3:
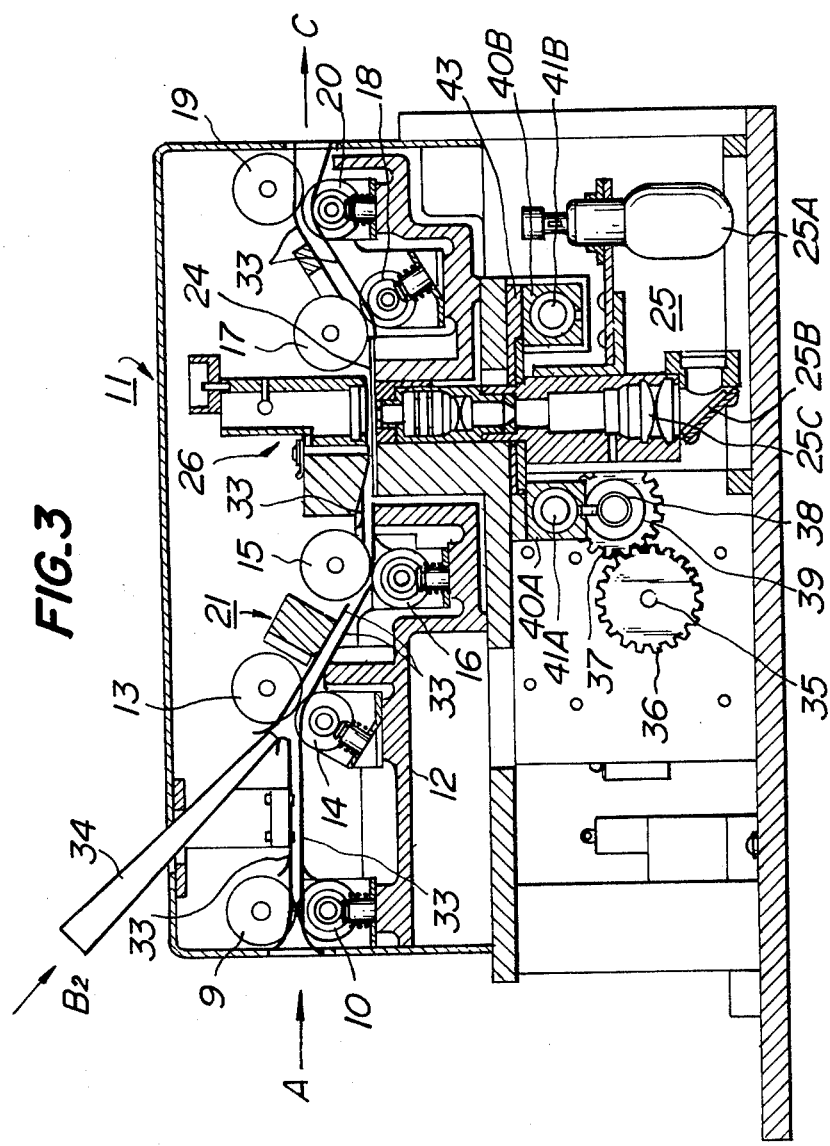
FIG. 3 is a cross section of an embodiment of the densitometer section.

FIG. 1 is a plan view showing an embodiment of a densitometer calibrating film according to the invention. The calibration film 1 has substantially the same configuration as the usual film for bearing a sample, such as serum. The calibration film 1 comprises a sheet 2 made of transparent and flexible material. There are formed identifying marks 3 and 4 at the front and rear edges, respectively, of the sheet 2. In the center of the substrate sheet 2 there are formed more a plurality of detection patterns 5 of known densities. In order to obtain good contact between the film 1 and rollers for feeding the film there are provided non-skid tracks 6 and 7 along side edges of the film 1. These tracks may be processed by a knurling tool.

FIG. 2 is a schematic view illustrating a densitometer section of a cataphoretic apparatus for which densitometer the calibration is effected using the calibration film shown in FIG. 1. In an automatic cataphoretic apparatus the usual serum bearing film is fed from a colorizing, decolorizing and drying secion 8 to a densitometer section 11 by means of driving rollers 9 and 10. The densitometer section 11 comprises a vessel 12 for containing a liquid for clarifying the serum bearing film having fractionated images. The serum bearing film is fed by means of four pairs of rollers 13, 14; 15, 16; 17, 18 and 19, 20 through the clarifying liquid. Behind the rollers 13 and 14 there is arranged a detector unit 21 for photoelectrically detecting the film and an output from the detector unit is supplied to a control circuit 22 which controls a motor 23 for driving the rollers so as to transport the film to a given position at a given velocity.

At the middle of the vessel 12 is provided a transparent window 24 and on each side of the window are arranged a light source unit 25 and a light receiving unit 26 which are movable in a direction perpendicular to the plane of the drawing of FIG. 2. In order to move the light source unit 25 there is provided a driving circuit 27 for controlling a motor 28 to which a pinion 29 is connected. The pinion 29 is engaged with a rack 30 secured to the light source unit 25. The light receiving unit 26 is also driven in synchronism with the light source unit 25 by means of a suitable driving mechanism so as to scan the film in its width direction. After the densitometric measurement is completed the film is discharged from the densitometer section 11 by means of the rollers 17 to 20. As explained above the usual sample bearing film is introduced into the densitometer section in the direction shown by an arrow A and is discharged from the densitometer section 11 in the direction shown by an arrow C.

According to the invention the calibration film 1 is introduced into the densitometer section 11 and is discharged after the calibration using the driving mechanism for transporting the usual sample bearing films. To this end, the calibration film 1 is supplied to the densitometer section 11 in the direction A or $B_1$ by means of the rollers 9 and 10 or on the direction $B_2$ by means of rollers 31 and 32. The calibration film 1 introduced into the densitometer section 11 is fed by the rollers 13 and 14 and the front mark 3 is detected by the detector unit 21. The unit 21 supplies a signal to the control circuit 22 and actuates a timer therein so as to energize the motor 23 for a given time period. This time period is so selected that the motor 23 is stopped when the pattern 5 of the calibration film 1 reaches the photoelectrically detecting position, i.e. an optical axis of the light source unit 25. At this position the calibration film 1 is scanned and measured by the light source unit 25 and the light receiving unit 26. The unit 26 receives a light ray passing through the pattern 5 and produces an electrical signal representing the density of the pattern 5. The calibration for a measuring circuit can be carried out by supplying the electrical signal to the circuit in such a manner that the measuring circuit indicates a density value which is identical with the known density of the pattern 5 of the calibration film 1. When the calibration film 1 has a plurality of patterns 5 as shown in FIG. 1, after the calibration for a first pattern has been completed, the film 1 is fed by a pattern pitch P and then the calibration for the next pattern is effected. In this manner the calibration can be carried out for successive patterns 5 of the calibration film 1. After the calibration with all patterns 5 has been finished, the calibration film 1 is discharged from the densitometer section 11 by means of the rollers 17 to 20 which are used to discharge the usual sample bearing films.

FIG. 3 is a cross section showing an embodiment of the densitometer section 11 in greater detail. In FIG. 3 those parts which are same as those in FIG. 2 are denoted by the same reference numerals as in FIG. 2. Along the path through which the serum bearing film and calibration film are to be fed are arranged a plurality of guide plates 33. The calibration film may be also introduced into the densitometer section in the direction $B_2$ by means of a duct 34. In a manual operation of the cataphoretic apparatus the serum bearing film may be also introduced into the section 11 through the duct 34. The light source unit 25 comprises a lamp 25A, a mirror 25B, and lens systems 25C and 25D. A mechanism for driving the light source unit 25 and light receiving unit 26 in the direction perpendicular to the plane of the drawing of FIG. 3 comprises a motor having a driving shaft 35, a gear 36 connected to the shaft 35, a gear 37 engaged with the gear 36, a feed screw 38 secured to the gear 37 and a feed nut 39 which travels along the feed screw 38. The feed nut 39 is coupled with a block 40A which is slidably supported by a guide rod 41A. A frame 43 of the light source unit 25 is connected to the block 40A. When the motor shaft 35 rotates, the block 40A and thus the light source unit 25 moves along the guide rod 41A. To the frame 43 is also secured a block 40B which is slidably supported by a guide rod 41B and the light receiving unit 26 is secured to the block 40B. Therefore the light receiving unit 26 moves in synchronism with the light source unit 25.

Figure 4:
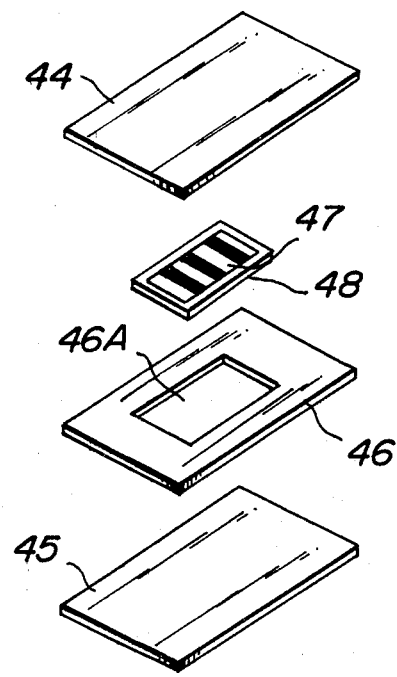
FIG. 4 is an exploded perspective view showing another embodiment of the calibration film according to the invention.

FIG. 4 is an exploded perspective view showing another embodiment of the calibration film according to the invention. In the calibrating method of the invention since the calibration film is immersed in the clarifying liquid the film should be protected against such a liquid. Further the exposed patterns are liable to be deteriorated or damaged. The calibration film shown in FIG. 4 is of a laminated construction and comprises upper and lower sheets 44 and 45 made of transparent and flexible material such as polyester, nylon, vinyl chloride, an intermediate frame 46 having a rectangular central opening 46A formed therein, and patterns 47 applied on a base 48. The base 48 having the patterns 44 of known density is inserted into the opening 46A and the sheets 44 and 45 and the frame 46 are cemented together with the aid of cementing agent so as to form the calibration film of laminated construction.

Figure 5:
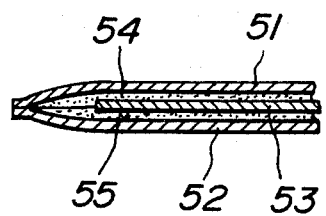
FIG. 5 is a cross section depicting still another embodiment of the calibration film according to the invention.

FIG. 5 is a cross section depicting still another embodiment of the calibration film according to the invention. In this embodiment the film comprises transparent upper and lower sheets 51 and 52, and a pattern 53 interposed between the sheets by means of adhesive layers 54 and 55 of hot melt resin mainly consisting of polyethylene.

It should be noted that the present invention is not limited to the embodiments explained above and many modifications are possible within the scope of the invention. For example in the calibration film shown in FIG. 1 the marks 3 and 4 are provided in order to bring the pattern 5 of the film 1 coincident with an optical axis of the light source unit 25 and the light receiving unit 26. However these marks may be dispensed with and the edge of the calibration film is detected and the patterns may be positioned at the given position. Further it is also possible to situate the patterns at the measuring position by placing the calibration film at a given marked position at the entrance of the densitometer section or to stop the front edge of the film by means of a stopper at the given position.

According to the invention it is possible to carry out the calibration for the densitometer without decomposing the densitometer nor drawing out the clarifying liquid. Thus the calibration can be performed easily and efficiently. Further the calibration film can be fed by means of the existent mechanism for feeding the usual sample bearing films without providing an additional mechanism and thus the calibration can be effected economically.

What is claimed is:

1. A method for calibrating a densitometer of an automatic cataphoresis apparatus including a vessel for containing a clarifying liquid for clarifying a sample bearing film, a photoelectric device for detecting a cataphoretic fractionate image on the sample bearing film situated at a measuring position in the clarifying liquid to produce an electrical signal relating to a density of the cataphoretic fractionate image, a measuring circuit for receiving said electrical signal; means for feeding the sample bearing film to said measuring position and means for discharging the sample bearing film from the measuring position, said method comprising:
    introducing a calibration film having standard patterns of known density sandwiched between upper and lower flexible and transparent sheets and an identifying mark into the densitometer by means of said feeding means, but through a path different from the path through which the sample bearing film is introduced, detecting the calibration film with the aid of the identification mark to set it at the measuring position, detecting photoelectrically the standard patterns on the calibration film by means of the photoelectric device to produce a standard electrical signal which is used to calibrate the measuring circuit, the photoelectric device in a direction perpendicular to the traveling direction of the film during moving calibration, and discharging the calibration film from the densitometer by means of said discharging means through the same path as that of the sample bearing film.

2. A method as claimed in claim 1 wherein said film is introduced between said upper and lower sheets in a liquid-tight manner.

3. A method as claimed in claim 2 wherein said standard patterns have a configuration which is substantially the same as the fractionate image on the sample bearing film.

4. A method as claimed in claim 2 comprising forming at least one of the upper and lower sheets with non-skid tracks along the side edges thereof.

5. A method as claimed in claim 2 wherein said calibration film with the standard patterns applied thereon is fitted in an opening provided in an intermediate frame sandwiched between the upper and lower sheets.

* * * * *